United States Patent
Su et al.

(10) Patent No.: US 10,167,246 B2
(45) Date of Patent: Jan. 1, 2019

(54) PREPARATIVE METHOD FOR CARBOXYLIC ACIDS

(71) Applicant: ZHEJIANG ZHUJI UNITED CHEMICALS CO., LTD, Hangzhou, Zhejiang (CN)

(72) Inventors: Yehua Su, Zhejiang (CN); Jieping Shi, Zhejiang (CN); Jianxin Lu, Zhejiang (CN); Tianhao Zhang, Zhejiang (CN); Xiaohua Yu, Zhejiang (CN); Guoping Cai, Zhejiang (CN); Bangchi Chen, Zhejiang (CN)

(73) Assignee: ZHEJIANG ZHUJI UNITED CHEMICALS CO., LTD, Hangzhou, Zhejiang (CN)

( * ) Notice: Subject to any disclaimer, the term of this patent is extended or adjusted under 35 U.S.C. 154(b) by 0 days.

(21) Appl. No.: 15/532,957

(22) PCT Filed: Sep. 25, 2015

(86) PCT No.: PCT/CN2015/090740
§ 371 (c)(1),
(2) Date: Jun. 2, 2017

(87) PCT Pub. No.: WO2016/086710
PCT Pub. Date: Jun. 9, 2016

(65) Prior Publication Data
US 2017/0369412 A1 Dec. 28, 2017

(30) Foreign Application Priority Data
Dec. 2, 2014 (CN) .......................... 2014 1 0724646

(51) Int. Cl.
| | | |
|---|---|---|
| *C07B 41/08* | (2006.01) |
| *C07C 53/08* | (2006.01) |
| *C07C 201/12* | (2006.01) |
| *C07C 205/11* | (2006.01) |
| *C07C 205/56* | (2006.01) |
| *C07C 205/58* | (2006.01) |
| *C07C 253/30* | (2006.01) |
| *C07C 255/41* | (2006.01) |
| *C07C 315/04* | (2006.01) |
| *C07C 317/44* | (2006.01) |
| *C07C 51/285* | (2006.01) |
| *C07D 213/60* | (2006.01) |
| *C07D 213/79* | (2006.01) |
| *C07D 213/803* | (2006.01) |

(52) U.S. Cl.
CPC ............ *C07C 51/285* (2013.01); *C07B 41/08* (2013.01); *C07C 53/08* (2013.01); *C07C 201/12* (2013.01); *C07C 205/58* (2013.01); *C07C 253/30* (2013.01); *C07C 315/04* (2013.01); *C07C 317/44* (2013.01); *C07D 213/60* (2013.01); *C07D 213/79* (2013.01); *C07D 213/803* (2013.01)

(58) Field of Classification Search
CPC ..... C07B 41/08; C07C 201/12; C07C 205/58; C07C 253/30; C07C 315/04; C07C 317/44; C07C 51/285; C07C 53/08; C07D 213/60; C07D 213/79; C07D 213/803
See application file for complete search history.

(56) References Cited

FOREIGN PATENT DOCUMENTS

CN          1239092          * 12/1999

OTHER PUBLICATIONS

English translation of CN1239092, Dec. 22, 1999, pp. 1-4 (Year: 1999).*

* cited by examiner

*Primary Examiner* — Pancham Bakshi
*Assistant Examiner* — Mark R Luderer

(57) ABSTRACT

A preparative method for carboxylic acids is disclosed in the present invention. The method is characterized in that: compounds (II) are reacted in the presence of hydrogen peroxide and base to produce target products (I), as represented by the following reaction scheme: wherein $R^1$ is aryl, pyridyl, pyrimidyl, pyridazinyl, pyrazinyl, benzothienyl, benzofuranyl, quinolinyl, isoquinolinyl, thiadiazolyl, $C_{1-6}$ alkyl, $C_{3-6}$ cycloalkyl, $C_{2-6}$ alkenyl, $C_{2-6}$ alkynyl and hydrogen; $R^2$ is alkoxycarbonyl, alkylaminocarbonyl, aminocarbonyl, alkylthiolcarbonyl, cyano, sulfonyl, sulfinyl, carbonyl, aldehyde, carboxyl, nitro, alkyl and hydrogen; $R^3$ is alkoxycarbonyl, alkyl amido carbonyl, aminocarbonyl, cyano, sulfonyl, sulfinyl, carbonyl, carboxyl and nitro. The present invention has the following main benefits: cheap and readily available starting materials, safe processes, high yield, good quality, which facilitates industrial production.

10 Claims, No Drawings

PREPARATIVE METHOD FOR CARBOXYLIC ACIDS

CROSS REFERENCE OF RELATED APPLICATION

This is a U.S. National Stage under 35 U.S.C 371 of the International Application PCT/CN2015/090740, filed Sep. 25, 2015, which claims priority under 35 U.S.C. 119(a-d) to CN 201410724646.4, filed Dec. 2, 2014.

BACKGROUND OF THE PRESENT INVENTION

Field of Invention

The present invention relates to a preparative method of organic compounds, and more particularly to a preparative method for carboxylic acids.

Description of Related Arts

Carboxylic acids are a class of important organic compounds which are widely applied in pesticide, veterinary drugs, medicine industry, and etc. For examples, 4-methanesulfonyl-2-nitrobenzoic acid is a key intermediate in synthesis of Mesotrione, and 4-trifluoromethyl-2-nitrobenzoic acid is a key intermediate in synthesis of Isoxaflutole.

The methods for synthesis of organic acids comprise hydrolysis of carboxylic acid derivatives, haloform reaction, cyano group hydrolysis, oxidation of alcohols or aldehydes, oxidation of alkanes, reaction of carbon dioxide with organo metalic salts.

Carboxylic acid derivatives include esters, amides and acyl chlorides, which are able to prepare carboxylic acid through hydrolysis under alkalic conditions. The yield of this preparative method is moderate to good, and is greatly affected by substrate. Also this preparative method requires pre-introduction of the carboxylic acid derivative functional groups. The method has certain limitation in application.

Haloform reaction is a reaction that a methyl ketone-containing substrate reacts with halogens to produce trihalomethyl ketone. Trihalomethyl ketone then undergoes hydrolysis to produce carboxylic acid. This preparative method has limited reaction applicability due to requirement of specifically structured substrate, and at the meantime produces large quantity of by-products.

Hydrolysis of cyano group under alkalic or acidic conditions is another method for preparing carboxylic acids. For example, o-nitrobenzonitrile undergoes hydrolysis to produce o-nitrobenzoic acid. U.S. Pat. No. 4,868,333 disclosed a method for hydrolyzing 4-trifluoromethyl-2-nitrobenzonitrile to 4-trifluoromethyl-2-nitrobenzoic acid using hydrobromic acid at >100° C. CN101575308 disclosed a method for hydrolyzing 4-trifluoromethyl-2-nitrobenzonitrile to 4-trifluoromethyl-2-nitrobenzoic acid in a good yield using sodium hydroxide in ethylene glycol at <140° C. But the synthesis of the 4-trifluoromethyl-2-nitrobenzonitrile starting material used in the two hydrolysis methods is difficult, which is usually produced by using highly toxic cyanating reagent such as sodium cyanide or copper cyanide to react with 4-trifluoromethyl-2-nitro-halobenzene (CN102675151, EP0994099, EP0758643, U.S. Pat. No. 5,705,674). The yield of the preparative method is not only low yielding with many impurities, but also using highly toxic cyanating reagent resulting in unsafe processing, high production cost and high volumn of industrial wastes.

Another preparative method for carboxylic acids is oxidation of alcohols or aldehydes. Tetrahedron Letters, 2008, 49(15), 2457-2460 reported a method of oxidizing o-nitrobenzyl alcohol with peroxybutanol catalyzed by copper(I) chloride in acetonitrile. WO2003033480 disclosed a method for obtaining o-nitrobenzoic acid using 2-nitrobenzaldehyde via oxidation using sodium perborate in acetic acid. However, the starting material in this process is difficult to obtain.

Benzoic acids is able to be prepared by oxidation of alkyl groups on benzene rings, the oxidizing agent used herein is usually air, potassium permanganate or nitric acid. U.S. Pat. No. 5,591,890 disclosed a method for preparing 4-methanesulfonyl-3-nitrobenzoic acid by oxidizing 4-methanesulfonyl-3-nitrotoluene with air under high pressure, wherein cobalt salt is used as catalyst and acetaldehyde as co-catalyst. CN1090843 disclosed another method for preparing methanesulfonyl-benzoic acid, by oxidizing methanesulfonyl-toluene with nitric acid and air in sulfuric acid in the presence of vanadium or cobalt compounds at 130° C.-170° C. The starting material in this process is not easy to obtain, the methyl group in the starting material is not ready to be oxidized, requiring harsh oxidation conditions, leading to poor oxidation selectivity and low yield.

Another preparative method for benzoic acids is the reaction of o-substituted benzene metal salts with carbon dioxide. Chemische Berichte,1986,119(6),1845-56 reported a method for preparing o-nitrobenzoic acid by reaction between o-nitro-phenyl lithium and carbon dioxide in tetrahydrofuran at low temperature. This reaction is low yielding, due to the interfering of the o-substituted group. Although, this method has its academic values, it is not amenable for industrial production.

In summary, while there are numerous methods reported for the preparation of carboxylic acids, they all have certain problems, limiting their applications, especially in the applications in the field of industrial production.

SUMMARY OF THE PRESENT INVENTION

The objectives of the present invention are to overcome the shortages of the conventional technologies and provide a convenient, safe, environmentally-friendly preparative method for carboxylic acids.

A preparative method for carboxylic acids, wherein compounds (II) are reacted in the presence of hydrogen peroxide and base to produce target products (I), as represented by the following reaction scheme:

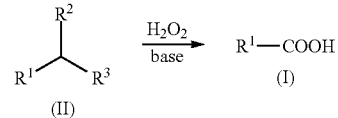

wherein $R^1$ is aryl, pyridyl, pyrimidyl, pyridazinyl, pyrazinyl, benzothienyl, benzofuranyl, quinolinyl, isoquinolinyl, thiadiazolyl, $C_{1-6}$ alkyl, $C_{3-6}$ cycloalkyl, $C_{2-6}$ alkenyl, $C_{2-6}$ alkynyl and hydrogen; $R^2$ is alkoxycarbonyl, alkylaminocarbonyl, aminocarbonyl, alkylthiolcarbonyl, cyano, sulfonyl, sulfinyl, carbonyl, aldehyde, carboxyl, nitro, alkyl and hydrogen; $R^3$ is alkoxycarbonyl, alkylaminocarbonyl, aminocarbonyl, cyano, sulfonyl, sulfinyl, carbonyl, carboxyl and nitro. $R^1$ is optimally aryl and pyridyl; $R^2$ is optimally alkoxycarbonyl, alkylaminocarbonyl, aminocarbonyl and cyano; $R^3$ is optimally cyano and alkoxycarbonyl. $R^1$ is optimally $C_6$-$C_{10}$ aryl and pyridyl; $R^2$ is optimally alkoxycarbonyl and aminocarbonyl; $R^3$ is optimally cyano. $R^1$ is optimally aryl and pyridyl which are substituted by ortho electron-withdrawing group; $R^2$ is optimally alkoxycarbonyl. Compounds (II) are further optimally ethyl 2-cyano-2-(2-nitro-4-(trifluoromethyl)phenyl)acetate, ethyl 2-cyano-2-(4-(methylsulfonyl)-2-nitrophenyl)acetate, ethyl 2-cyano-2-(2-(methylsulfonyl)-4-(trifluoromethyl)phenyl)acetate, methyl 2-cyano-2-(2-nitro-4-(trifluoromethyl)phenyl)acetate, methyl 2-cyano-2-(4-(methylsulfonyl)-2-nitrophenyl)acetate, methyl 2-cyano-2-(2-(methylsulfonyl)-4-(trifluoromethyl)phenyl)acetate, isopropyl 2-cyano-2-(2-nitro-4-(trifluoromethyl)phenyl)acetate, isopropyl 2-cyano-2-(4-(methylsulfonyl)-2-nitrophenyl)acetate, isopropyl 2-cyano-2-(2-(methylsulfonyl)-4-(trifluoromethyl)phenyl)acetate, 2-cyano-2-(2-nitro-4-(trifluoromethyl)phenyl)acetamide, 2-cyano-2-(2-nitro-4-(methanesulfonyl)phenyl)acetamide, 2-cyano-2-(2-(methylsulfonyl)-4-(trifluoromethyl)phenyl) acetamide.

The base comprises inorganic base and organic base; the molar ratio of the base and compounds (II) is optimally 1:1-3:1, wherein the inorganic base is optimally alkali metal carbonate, alkali metal hydroxide, alkaline earth metal carbonate, alkaline earth metal hydroxide, alkali metal acetate, alkali metal formate, alkali metal alkoxide; the organic base is optimally quaternary ammonium hydroxide, quaternary phosphonium hydroxide and organic amine. Wherein the inorganic base is further optimally potassium carbonate, sodium hydroxide and potassium hydroxide. The oxidation reaction solvent is water or water-soluble organic solvent. The oxidation reaction solvent is further optimally selected from the group consisting of water, DMF (dimethylformamide), NMP (N-methyl-2-pyrrolidone), DMSO (dimethyl sulfoxide), methanol, ethanol, acetonitrile and THF (tetrahydrofuran). The molar ratio of the base and compounds (II) is 1:1-4:1. The molar ratio of the base and compounds (II) is further optimally 1:1-3:1. The molar ratio of the oxidation agent and compounds (II) is optimally 2:1-8:1. The molar ratio of the oxidation agent and compounds (II) is further optimally 2:1-5:1. The temperature required by the oxidation reaction is optimally −20-80° C.; the temperature required by the oxidation reaction is further optimally 0-60° C. The reaction product is in carboxylate form. An acid is required for the acidification during the workup. After usual workup, carboxylic acid compound is obtained.

Compounds (II) is able to be conveniently obtained, prepared with a number of conventional methods. For example, compounds (II) are produced by reaction of compounds (III) and compounds (IV) in the presence of base:

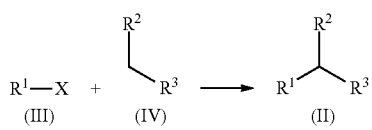

wherein $R^1$, $R^2$ and $R^3$ are defined as the same as the defination for compounds (II). X is fluoro, chloro, bromo, iodo, nitro, methanesulfonyl and methanesulfinyl.

The base comprises generally inorganic base and organic base. The base is optimally alkali metal carbonate, alkali metal hydroxide, alkaline earth metal carbonate, alkaline earth metal hydroxide, alkali metal acetate, alkali metal formate, alkali metal alkoxide, quaternary ammonium hydroxide, quaternary phosphonium hydroxide. The base is further optimally selected from a group consisting of potassium carbonate, sodium hydroxide, potassium hydroxide, sodium ethoxide, sodium methoxide, tetraalkyl ammonium hydroxide and sodium acetate. The base is further optimally potassium carbonate, sodium hydroxide, potassium hydroxide. The molar ratio of the base and compounds (II) is optimally 1:1-5:1. The molar ratio of the base and compounds (II) is further optimally 1:1-2.5:1.

Compounds (II) is able to be prepared by a metal catalyzed coupling reaction.

Compared with the conventional technologies, the present invention has the following benefits:

The reactive center carbon atom is mildly oxidized by hydrogen peroxide under alkalic conditions to give rise to carboxylic acid. The reaction is environmentally-friendly and safe. The starting material is cheap and readily available. The yield is high and the product is of high purity.

DETAILED DESCRIPTION OF THE PREFERRED EMBODIMENT

A preparative method for carboxylic acids, wherein compounds (II) are reacted in the presence of hydrogen peroxide and base to produce target products (I), as represented by the following reaction scheme:

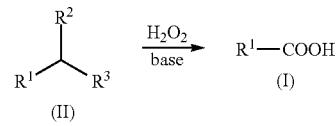

wherein $R^1$ is aryl, pyridyl, pyrimidyl, pyridazinyl, pyrazinyl, benzothienyl, benzofuranyl, quinolinyl, isoquinolinyl, thiadiazolyl, $C_{1-6}$ alkyl, $C_{3-6}$ cycloalkyl, $C_{2-6}$ alkenyl, $C_{2-6}$ alkynyl and hydrogen; $R^2$ is alkoxycarbonyl, alkylaminocarbonyl, aminocarbonyl, alkylthiolcarbonyl, cyano, sulfonyl, sulfinyl, carbonyl, aldehyde, carboxyl, nitro, alkyl and hydrogen; $R^3$ is alkoxycarbonyl, alkylaminocarbonyl, aminocarbonyl, cyano, sulfonyl, sulfinyl, carbonyl, carboxyl and nitro. $R^1$ is optimally aryl and pyridyl; $R^2$ is optimally alkoxycarbonyl, alkylaminocarbonyl, aminocarbonyl and cyano; $R^3$ is optimally cyano and alkoxycarbonyl. $R^1$ is optimally $C_6$-$C_{10}$ aryl and pyridyl; $R^2$ is optimally alkoxycarbonyl and aminocarbonyl; $R^3$ is optimally cyano. $R^1$ is optimally aryl and pyridyl which are substituted by ortho electron-withdrawing group; $R^2$ is optimally alkoxycarbonyl. Compounds (II) are further optimally ethyl 2-cyano-2-(2-nitro-4-(trifluoromethyl)phenyl)acetate, ethyl 2-cyano-2-(4-(methylsulfonyl)-2-nitrophenyl)acetate, ethyl 2-cyano-2-(2-(methylsulfonyl)-4-(trifluoromethyl)phenyl)acetate, methyl 2-cyano-2-(2-nitro-4-(trifluoromethyl)phenyl)acetate, methyl 2-cyano-2-(4-(methylsulfonyl)-2-nitrophenyl) acetate, methyl 2-cyano-2-(2-(methylsulfonyl)-4-(trifluoromethyl)phenyl)acetate, isopropyl 2-cyano-2-(2-nitro-4-(trifluoromethyl)phenyl)acetate, isopropyl 2-cyano-2-(4-(methylsulfonyl)-2-nitrophenyl)acetate, isopropyl 2-cyano-2-(2-(methylsulfonyl)-4-(trifluoromethyl)phenyl)acetate, 2-cyano-2-(2-nitro-4-(trifluoromethyl)phenyl)acetamide, 2-cyano-2-(2-nitro-4-(methanesulfonyl)phenyl)acetamide, 2-cyano-2-(2-(methylsulfonyl)-4-(trifluoromethyl)phenyl) acetamide.

The base comprises inorganic base and organic base; the molar ratio of the base and compounds (II) is optimally 1:1-3:1, wherein the inorganic base is optimally alkali metal carbonate, alkali metal hydroxide, alkaline earth metal carbonate, alkaline earth metal hydroxide, alkali metal acetate, alkali metal formate, alkali metal alkoxide; the organic base is optimally quaternary ammonium hydroxide, quaternary phosphonium hydroxide and organic amine. Wherein the inorganic base is further optimally potassium carbonate, sodium hydroxide and potassium hydroxide. The oxidation reaction solvent is water or water-soluble organic solvent. The oxidation reaction solvent is further optimally selected from the group consisting of water, DMF (dimethylformamide), NMP (N-methyl-2-pyrrolidone), DMSO (dimethyl sulfoxide), methanol, ethanol, acetonitrile and THF (tetrahydrofuran). The molar ratio of the base and compounds (II) is 1:1-4:1. The molar ratio of the base and compounds (II) is further optimally 1:1-3:1. The molar ratio of the oxidation agent and compounds (II) is optimally 2:1-8:1. The molar ratio of the oxidation agent and compounds (II) is further optimally 2:1-5:1. The temperature required by the oxidation reaction is optimally −20-80° C.; the temperature required by the oxidation reaction is further optimally 0-60° C. The reaction product is in carboxylate form. An acid is required for the acidification during the workup. After usual workup, carboxylic acid compound is obtained.

Compounds (II) can be conveniently obtained, prepared with a number of conventional methods. For example, compounds (II) are produced by reaction of compounds (III) and compounds (IV) in the presence of base:

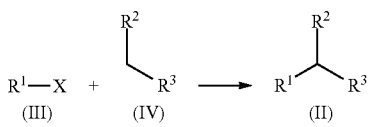

wherein $R^1$, $R^2$ and $R^3$ are defined as the same as the defination for compounds (II). X is fluoro, chloro, bromo, iodo, nitro, methanesulfonyl and methanesulfinyl.

The base comprises inorganic base and organic base. The base is optimally alkali metal carbonate, alkali metal hydroxide, alkaline earth metal carbonate, alkaline earth metal hydroxide, alkali metal acetate, alkali metal formate, alkali metal alkoxide, quaternary ammonium hydroxide, quaternary phosphonium hydroxide. The base is further optimally selected from a group consisting of potassium carbonate, sodium hydroxide, potassium hydroxide, sodium ethoxide, sodium methoxide, tetraalkyl ammonium hydroxide and sodium acetate. The base is further optimally potassium carbonate, sodium hydroxide, potassium hydroxide. The molar ratio of the base and compounds (II) is optimally 1:1-5:1. The molar ratio of the base and compounds (II) is further optimally 1:1-2.5:1.

Compounds (II) can also be prepared by a metal catalyzed coupling reaction.

The following embodiments are used to further illustrate some features of the present invention, they should not be considered to be limitations to the claims of the present invention.

Embodiment 1: Preparation of 2-nitro-4-trifluoromethylbenzoic acid.

To a 100 mL three-necked flask equipped with a thermometer was added 10 g 3-nitro-4-(nitromethyl)trifluorotoluene, 11 g potassium carbonate and 40 g DMSO (dimethyl sulfoxide). The mixture was stirred and heated to 70° C. 16 g hydrogen peroxide (30%) was added dropwise. The reaction was continued for 1 hour. After the reaction was complete, the mixture was cooled, diluted with a certain amount of water, acidified with hydrochloric acid, filtered by vacuum suction, washed with water, dried to produce 8.3 g 2-nitro-4-trifluoromethylbenzoic acid as a solid in 88% yield. $^1$H-NMR δppm(DMSO-$d_6$): 14.39(br, 1H), 8.46(s, 1H), 8.21(d, J=8.0 Hz, 1H), 8.09(d, J=8.0 Hz, 1H).

Embodiment 2: preparation of 2-nitro-4-methanesulfonylbenzoic acid.

To a 1000 mL three-necked flask equipped with a thermometer was added 100 g diethyl 2-nitro-4-methanesulfonylphenyl malonate, 30 g sodium hydroxide and 500 g DMF. The mixture was stirred and heated to 80° C. 105 g hydrogen peroxide (30%) was added dropwise. The reaction was continued for 2 hours. After the reaction was complete, the mixture was cooled, diluted with a certain amount of water, acidified with hydrochloric acid, filtered by vacuum suction, washed with water, dried to produce 62.4 g 2-nitro-4-methanesulfonylbenzoic acid as a solid in 88% yield. $^1$H-NMR δppm(DMSO-$d_6$): 14.42(br, 1H), 8.53(d, J=1.6 Hz, 1H), 8.33(dd, $J_1$=1.6 Hz $J_2$=8.0 Hz, 1H), 8.12 (d, J=8.0 Hz, 1H), 3.39 (s, 3H).

Embodiment 3: preparation of 2-nitro-4-methanesulfonylbenzoic acid.

To a 1000 mL three-necked flask equipped with a thermometer was added 143 g methyl 2-cyano-2-(4-(methylsulfonyl)-2-nitrophenyl)acetate, 60 g potassium hydroxide and 500 g water. The mixture was stirred and heated to 40° C. 200 g hydrogen peroxide (30%) was added dropwise. The reaction was continued for 2 hours. After the reaction was complete, the mixture was cooled, acidified with hydrochloric acid, filtered by vacuum suction, washed with water, dried to produce 114 g 2-nitro-4-methanesulfonyl benzoic acid as a solid in 97% yield.

Embodiment 4: preparation of a 2-nitro-4-trifluoromethylbenzoic acid.

To a 1000 mL three-necked flask equipped with a thermometer was added 131 g 2-cyano-2-(2-nitro-4-(trifluoromethyl)phenyl)acetamide, 65 g potassium hydroxide and 400 g water. The mixture was stirred and heated to 70° C. 210 g hydrogen peroxide (30%) was added dropwise. The reaction was continued for 2 hours. After the reaction was complete, the mixture was cooled, acidified with hydrochloric acid, filtered by vacuum suction, washed with water, dried to produce 107.5 g 2-nitro-4-methanesulfonyl benzoic acid as a solid in 95% yield.

Embodiment 5: preparation of 3,5,6-trichloropicolinic acid

To a 500 mL three-necked flask equipped with a thermometer was added 29.5 g ethyl 2-cyano-2-(3,5,6-trichloropyridin-2-yl)acetate, 20 g sodium acetate and 150 g water. The mixture was stirred and heated to 60° C. 25 g hydrogen peroxide (30%) was added dropwise. The reacting was continued for 1 hour. After the reaction was complete, the mixture was cooled down, acidified with hydrochloric acid, filtered by vacuum suction, washed with water, dried to produce 22.3 g 3,5,6-trichloropicolinic acid as a solid in 98% yield. $^1$H-NMR δppm(CDCl$_3$):14.30(br,1H), 8.61(s, 1H).

Embodiment 6: preparation of 3-chloro-5-(trifluoromethyl)picolinic acid.

To a 500 mL three-necked flask equipped with a thermometer was added 29.5 g ethyl 2-(3-chloro-5-(trifluoromethyl)pyridin-2-yl)-2-cyanoacetate, 15 g sodium hydroxide and 200 g water. The mixture was stirred and heated to 30° C. 30 g hydrogen peroxide (30%) was added dropwise. The reacting was continued for 1 hour. After the reaction was complete, the mixture was cooled down, acidified with hydrochloric acid, filtered by vacuum suction, washed with water, dried to produce 22.5 g 3-chloro-5-(trifluoromethyl) picolinic acid as a solid in 99% yield. $^1$H-NMR δppm (CDCl$_3$):14.40(br, 1H), 9.01(s, 1H), 8.65(s, 1H).

Embodiment 7: preparation of acetic acid

To a 500 mL three-necked flask equipped with a thermometer was added 29.8 g methyl 2-cyanopropanoate, 28 g sodium ethoxide and 200 g ethanol. The mixture was stirred and cooled to 0° C. 27 g hydrogen peroxide (50%) was added dropwise. The reaction was continued for 2 hours. After the reaction was complete, ethanol and water were distilled out. A certain amount of concentrated sulfuric acid was added and 11.5 g acetic acid was distilled out, and collected in 95% yield.

Embodiment 8: preparation of diethyl 2-(2-nitro-4-(trifluoromethyl) phenyl)malonate To a 1000 mL three-necked flask equipped with a thermometer was added 350 g DMF, 190 g potassium carbonate, 120 g sodium hydroxide and 200 g diethyl malonate.

150 g 1-chloro-2-nitro-4-(trifluoromethyl)benzene was added while the reaction temperature was controlled at 45° C. After addition, the reaction was continued for 1 hour. After the reaction was complete, the solvent was removed. Water was added. The mixture was acidified with hydrochloric acid, filtered, washed with water, dried to produce 227 g diethyl 2-(2-nitro-4-(trifluoromethyl)phenyl)malonate in 98% yield. $^1$H-NMR δppm(CDCl$_3$): 8.33(s, 1H), 7.91(d, J=8.0 Hz, 1H), 7.73 (d,J=8.0 Hz, 1H), 5.34(s, 1H), 4.30 (q, J=7.2 Hz, 4H), 1.30 (t, J=7.2 Hz, 6H).

Embodiment 9: preparation of 2-nitro-1-(nitromethyl)-4-(trifluoromethyl)benzene

To a 500 mL three-necked flask equipped with a thermometer was added 220 g NMP, 46 g sodium hydroxide and 35 g nitromethane. The mixture was stirred for 30 min at 5° C. 100 g 1-chloro-2-nitro-4-(trifluoromethyl)benzene was added slowly while the reaction temperature was controlled at 5° C. After addition, the reaction was continued for 2 hours. After the reaction was complete, the solvent was removed. Water was added. The mixture was acidified with hydrochloric acid, filtered, washed with water, dried to produce 107 g 2-nitro-1-(nitromethyl)-4-(trifluoromethyl) benzene in 98% yield. $^1$H-NMR δppm(CDCl$_3$):8.55(s, 1H), 8.03(d, J=8.0 Hz, 1H), 7.69(d, J=8.0 Hz, 1H), 5.91 (s, 2H).

Embodiment 10: Preparation of methyl 2-cyano-2-(4-(methylsulfonyl)-2-nitrophenyl)acetate To a 1000 mL three-necked flask equipped with a thermometer was added 400 g DMSO, 52 g sodium hydroxide and 64 g methyl 2-cyanoacetate. 150 g 4-methanesulfonyl-2-nitrochlorobenzene was added while the reaction temperature was controlled at 60° C. After addition, the reaction was continued for 1 hour. After the reaction was complete, the solvent was removed. Water was added. The mixture was acidified with hydrochloric acid, filtered, washed with water, dried to produce 182 g methyl 2-cyano-2-(4-(methylsulfonyl)-2-nitrophenyl)acetate in 96% yield. $^1$H-NMR δppm (CDCl$_3$):8.77(d, J=1.6 Hz, 1H), 8.33(dd, J$_1$=1.6 Hz J$_2$=8.0 Hz, 1H), 8.07 (d, J=8.0 Hz, 1H), 5.82(s, 1H), 3.90 (s, 3H), 3.17 (s, 3H).

Embodiment 11: preparation of ethyl 2-cyano-2-(2-nitro-4-(trifluoromethyl)phenyl)acetate To a 1000 mL three-necked flask equipped with a thermometer was added 500 g DMF, 150 g potassium carbonate and 77 g ethyl 2-cyanoacetate. 150 g 4-chlorine-3-nitro-trifluorotoluene was added while the reaction temperature was controlled within 50° C. After addition, the reaction was continued for 1 hour. After the reaction was complete, the solvent was removed. Water was added. The mixture was acidified with hydrochloric acid, filtered, washed with water, dried to produce 195 g ethyl 2-cyano-2-(2-nitro-4-(trifluoromethyl)phenyl)acetate in 97% yield. $^1$H-NMR δppm (CDCl$_3$):8.49(s, H), 8.03(d, J=8.0 Hz, 1H), 7.98 (d, J=8.0 Hz, 1H), 5.77(s, 1H), 4.33 (q, J=7.2 Hz, 2H), 1.34 (t, J=7.2 Hz, 3H).

Embodiment 12: preparation of ethyl 2-cyano-2-(3,5,6-trichloropyridin-2-yl)acetate To a 1000 mL three-necked flask equipped with a thermometer was added 500 g DMF, 80 g potassium carbonate and 59 g ethyl 2-cyanoacetate. 109 g 2,3,5,6-tetrachloro-pyridine and 150 g DMF were added while the reaction temperature was controlled within 50° C. After addition, the reaction was continued for 1 hour. After the reaction was complete, the solvent was removed. Water was added. The mixture was acidified with hydrochloric acid, filtered, washed with water, dried to produce 145 g ethyl 2-cyano-2-(3,5,6-trichloropyridin-2-yl)acetate in 98% yield. $^1$H-NMR δppm(CDCl$_3$): 14.61(b,1H), 8.53(s, 1H), 4.25(d, J=5.6 Hz, 2H), 1.2 (t, J=5.6 Hz, 3H).

Embodiment 13: preparation of ethyl 2-(3-chloro-5-(trifluoromethyl)pyridin-2-yl)-2-cyanoacetate To a 500 mL three-necked flask equipped with a thermometer was added 200 g DMSO, 25 g potassium hydroxide and 24 g ethyl 2-cyanoacetate. 44 g 2,3-dichloro-5-(trifluoromethyl)pyridine was added while the reaction temperature was controlled within 50° C. After addition, the reaction was continued for 1 hour. After the reaction was complete, the solvent was removed. Water was added. The mixture was acidified with hydrochloric acid, filtered, washed with water, dried to produce 85 g ethyl ethyl 2-(3-chloro-5-(trifluoromethyl)pyridin-2-yl)-2-cyanoacetate in 97% yield. $^1$H-NMR δppm(CDCl$_3$): 8.6(s, 1H), 6.27(s, 1H), 4.25(d, J=5.6 Hz, 2H), 3.40(br, 1H), 1.2 (t, J=5.6 Hz, 3H).

Embodiment 14: preparation of 2-cyano-2-(2-nitro-4-(trifluoromethyl)phenyl)acetamide To a 1000 mL three-necked flask equipped with a thermometer was added 450 g DMF, 50 g potassium hydroxide and 45 g 2-cyanoacetamide. 120 g 4-chlorine-3-nitro-trifluorotoluene was added while the reaction temperature was controlled within 30° C. After addition, the reaction was continued for 1 hour. After the reaction was complete, the solvent was removed. Water was added. The mixture was acidified with hydrochloric acid, filtered, washed with water, dried to produce 142 g 2-cyano-2-(2-nitro-4-(trifluoromethyl)phenyl)acetamide in 98% yield. $^1$H-NMR δppm (CDCl$_3$):8.48(s, 1H), 8.28(d, J=6.4 Hz, 1H), 8.09(s, 1H) 7.99 (d, J=6.4 Hz, 1H), 7.83 (s, 1H), 5.80(s, 1H).

What is claimed is:

1. A preparative method for carboxylic acids, wherein compounds (II) are reacted in the presence of hydrogen peroxide and base to produce target products (I), the reaction scheme is shown as below:

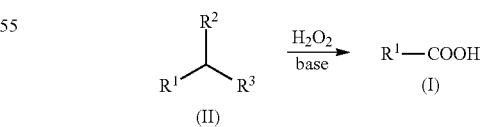

wherein R$^1$ is an aryl, a pyridyl, a pyrimidyl, a pyridazinyl, a pyrazinyl, a benzothienyl, a benzofuranyl, a quinolinyl, an isoquinolinyl, a thiadiazolyl, a C$_{1-6}$ alkyl, a C$_{3-6}$ cycloalkyl, a C$_{2-6}$ alkenyl, or C$_{2-6}$ alkynyl; R$^2$ is an alkoxycarbonyl, an alkylaminocarbonyl, an aminocarbonyl, an alkylthiolcarbonyl, a cyano, a sulfonyl, a sulfinyl, an aldehyde, or a nitro, R$^3$ is an alkoxycarbonyl, an alkyl amido carbonyl, an aminocarbonyl, a cyano, a sulfonyl, a sulfinyl, or a nitro.

2. The method as recited in claim 1, wherein the $R^1$ is the aryl or the pyridyl; the $R^2$ is the alkoxycarbonyl, an alkylaminocarbonyl, the aminocarbonyl or the cyano; $R^3$ is the cyano or the alkoxycarbonyl.

3. The method as recited in claim 1, wherein the $R^1$ is a $C_6$-$C_{10}$ aryl or the pyridyl; the $R^2$ is the alkoxycarbonyl or the aminocarbonyl; the $R^3$ is cyano.

4. The method as recited in claim 1, wherein the $R^1$ is the aryl or the pyridyl which are substituted by an ortho electron-withdrawing group; the $R^2$ is alkoxycarbonyl.

5. The method as recited in claim 1, wherein compounds (II) are further ethyl 2-cyano-2-(2-nitro-4-(trifluoromethyl) phenyl)acetate, ethyl 2-cyano-2-(4-(methyl sulfonyl)-2-nitrophenyl)acetate, ethyl 2-cyano-2-(2-(methyl sulfonyl)-4-(trifluoromethyl)phenyl)acetate, methyl 2-cyano-2-(4-(methyl sulfonyl)-2-nitrophenyl)acetate, methyl 2-cyano-2-(2-(methyl sulfonyl)-4-(trifluoromethyl)phenyl)acetate, isopropyl 2-cyano-2-(2-nitro-4-(trifluoromethyl)phenyl)acetate, isopropyl 2-cyano-2-(4-(methyl sulfonyl)-2-nitrophenyl)acetate, isopropyl 2-cyano-2-(2-(methyl sulfonyl)-4-(trifluoromethyl)phenyl)acetate, 2-cyano-2-(2-nitro-4-(trifluoromethyl)phenyl)acetamide, 2-cyano-2-(2-nitro-4-(methanesulfonyl)phenyl)acetamide, 2-cyano-2-(2-(methyl sulfonyl)-4-(trifluoromethyl)phenyl)acetamide.

6. The method as recited in claim 1, wherein the base comprises an inorganic base or an organic base; a molar ratio of the base and compounds (II) is 1:1-3:1.

7. The method as recited in claim 6, wherein the inorganic base is an alkali metal carbonates, an alkali metal hydroxide, an alkaline-earth metal carbonate, an alkaline earth metal hydroxide, an alkali metal acetate, an alkali metal formate, an alkali metal alkoxide; the organic base is a quaternaryammoniumhydroxide, quaternary phosphonium hydroxide or an organic amine.

8. The method as recited in claim 7, wherein the inorganic base is further a potassium carbonate, a sodium hydroxide or a potassium hydroxide.

9. The method as recited in claim 1, wherein the reaction takes place in a solvent, the solvent is selected from the group consisting of water, DMF(dimethylformamide), NMP (N-Methyl-2-pyrrolidone), DMSO(Dimethyl sulfoxide), methanol, an ethanol, an acetonitrile or a THF (Tetrahydrofuran).

10. The method as recited in claim 1, wherein the molar ratio of the hydrogen peroxide and the compounds (II) is 2:1-5:1; the temperature of oxidation reaction is 0-60° C.

* * * * *